United States Patent [19]

Riggin

[11] Patent Number: 4,484,133
[45] Date of Patent: Nov. 20, 1984

[54] MICROWAVE MOISTURE SENSOR

[75] Inventor: Michael T. Riggin, Downsview, Canada

[73] Assignee: Sentrol Systems Ltd., Downsview, Canada

[21] Appl. No.: 333,661

[22] Filed: Dec. 23, 1981

[51] Int. Cl.³ ............................................. G01R 27/04
[52] U.S. Cl. .............................. 324/58.5 A; 324/58.5 B
[58] Field of Search ............... 324/58.5 A, 58.5 B, 324/58.5 R

[56] References Cited

U.S. PATENT DOCUMENTS 3,622,874 11/1971 Chasek ........................ 324/58.5 A
3,815,019 6/1974 Wiles ............................ 324/58.5 A

FOREIGN PATENT DOCUMENTS 2361677 9/1974 Fed. Rep. of Germany ..... 324/58.5 A
1114157 5/1968 United Kingdom .......... 324/58.5 A
620878 8/1978 U.S.S.R. ........................ 324/58.5 A
636476 12/1978 U.S.S.R. ........................ 324/58.5 B
832430 5/1981 U.S.S.R. ........................ 324/58.5 A

OTHER PUBLICATIONS

Beyer et al., Microwave Thickness Detector, The Review of Scientific Instruments, Mar. 1960, pp. 313-316.

Primary Examiner—Stanley T. Krawczewicz
Attorney, Agent, or Firm—Shenier & O'Connor

[57] ABSTRACT

Microwave moisture measuring apparatus for on-line monitoring of a paper web in which a source of radiation is measured and directed towards the web. Detectors measure the transmitted and reflected energy, and a microcomputer, also having inputs in accordance with the temperature and weight of the web, provides an indication of the moisture content of the web.

10 Claims, 4 Drawing Figures

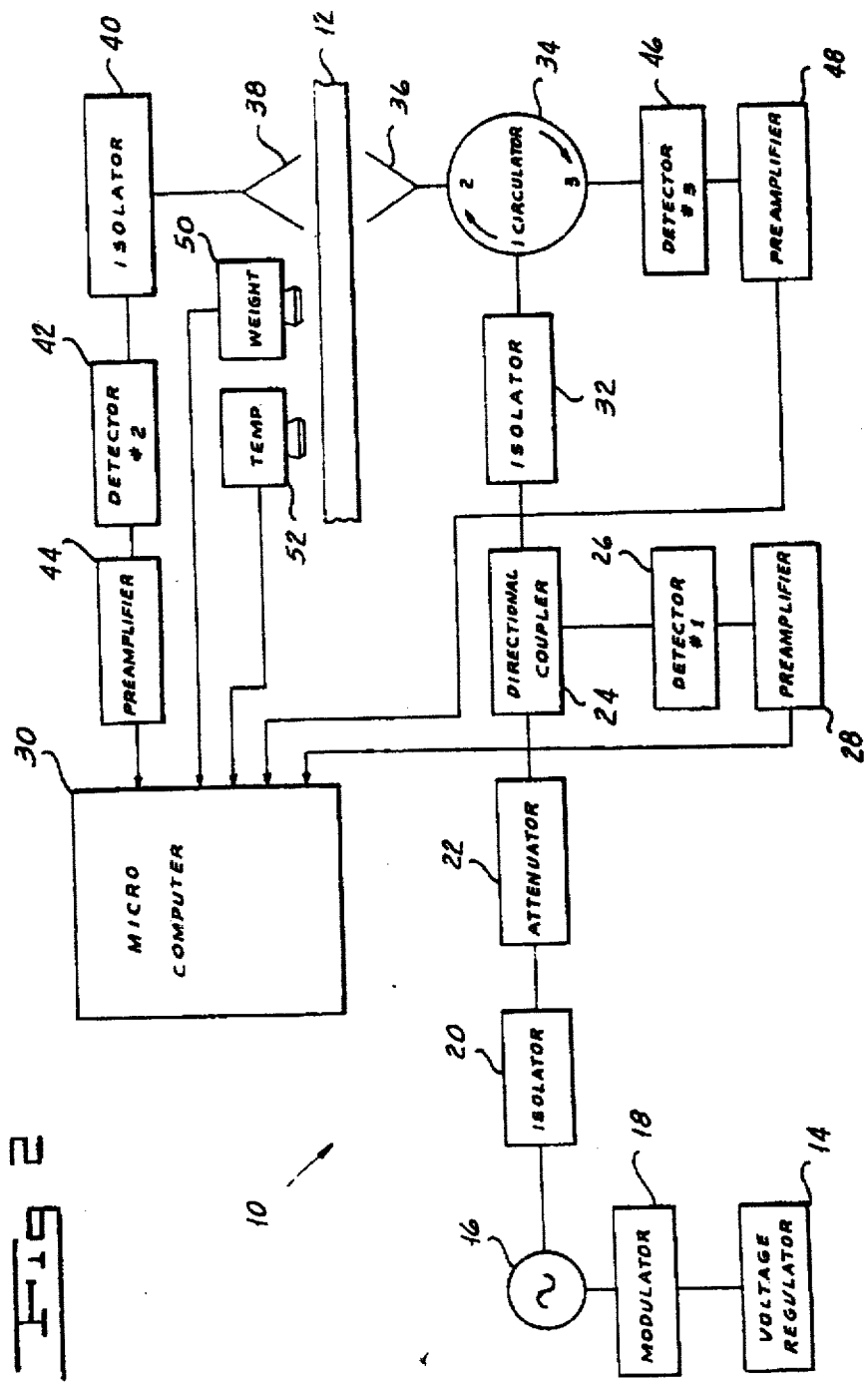

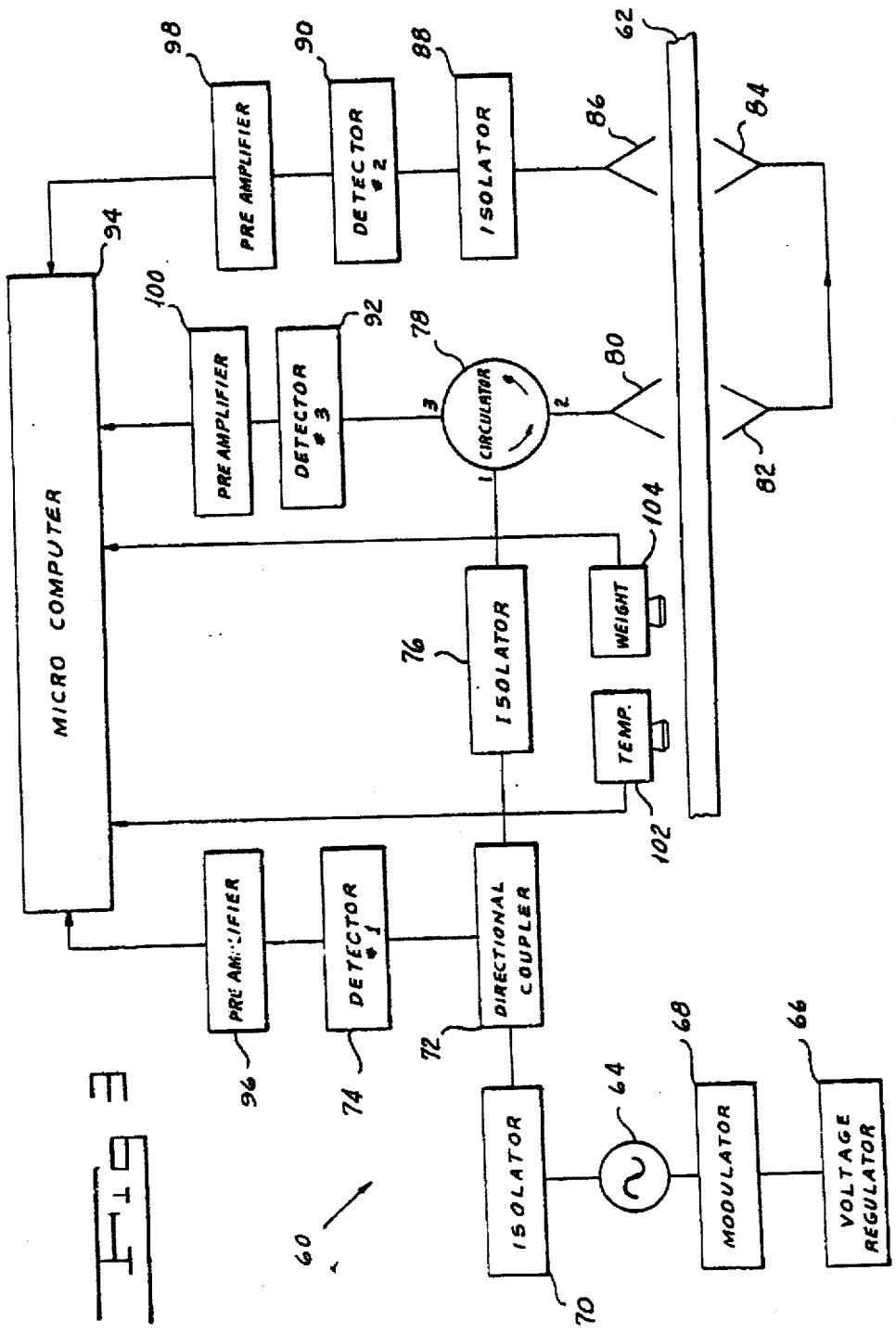

MICROWAVE MOISTURE SENSOR

FIELD OF THE INVENTION

My invention relates to the field of on-line microwave moisture sensors and more particularly to a sensor for measuring the moisture content of a moving web independent of its thickness.

BACKGROUND OF THE INVENTION

There are known in the prior art instruments for measuring the moisture content of a moving web in an on-line installation. In such instruments a microwave transmitting horn on one side of the web directs microwave energy at a frequency of about 22.2 GHz through the web to a receiving horn on the opposite side of the web. The signal output of the receiving horn is used to provide an indication of the moisture content in the web. One example of such a microwave moisture measuring instrument is disclosed in Mounce U.S. Pat. No. 3,851,244, issued Nov. 26, 1974. Other moisture measuring instruments are shown in Walker U.S. Pat. No. 3,693,079, Busker et al U.S. Pat. No. 3,681,684 and Walker U.S. Pat. No. 3,534,260. In these latter patents various devices are provided to prevent reflected radiation from returning to the transmitting horn effectively to augment or decrease the apparent power radiated from the sending horn.

In systems of the type discussed hereinabove, power P at the receiving horn is related to power Po from the sending horn by the relationship:

$$P/P_o = e^{-\alpha t} \quad (1)$$

where $\alpha$ is the attenuation constant and $t$ is the thickness of the attenuating medium. The attenuation constant of the web is given by:

$$\alpha = \frac{2\pi}{\lambda}\left(\frac{E'}{2}[[1 + (E''/E')^2]^{\frac{1}{2}} - 1]\right)^{\frac{1}{2}} \quad (2)$$

From the foregoing it will be seen that microwave moisture sensors of the prior art depend for their operation on the interaction of microwaves with the water in the web.

While microwave moisture measuring instruments of the prior art are generally satisfactory in providing an indication of the moisture content of a moving web, they suffer from a number of defects. They do not account for the effects on the radiation of properties of the web other than moisture content.

Microwaves couple to rotational degrees of freedom of water molecules which are hindered by interactions with the matrix or base material of the web and with other water molecules. For example, when the web is a cellulose product, water molecules bind to hydroxyl groups on the fiber. The bound water interacts differently with the radiation than the unbound water. Since the relative amount of bound to unbound water is determined by the equilibrium temperature of the web, the attenuation of radiation by the cellulose-water mixture is temperature dependent.

In addition to the interaction of the microwaves with water in the web, the radiation also interacts with the base matrix of the web so that the attenuation constant depends on the dry weight or dry mass per unit area of the web.

When the thickness of the web is near a multiple of one fourth the wavelength of the microwaves in the medium, reflection from the surface of the web results in a dependence of the attenuation constant on web thickness.

None of the moisture measuring systems of the prior art take into account the effects of web thickness on the attenuation constant with the result that the indications provided are not as accurate as is desired.

SUMMARY OF THE INVENTION

One object of my invention is to provide a microwave moisture sensor which provides accurate measurements of the moisture content of a moving web independent of its thickness.

Another object of my invention is to provide a microwave moisture sensor which compensates for the effect of variations in the basis weight and temperature of the web on the moisture measurement.

Still another object of my invention is to provide a microwave moisture sensor which is capable of measuring high moisture concentrations, above 750 grams per square meter and low moisture concentrations, below 5 grams per square meter in a moving web.

Other and further objects of my invention will appear from the following description.

BRIEF DESCRIPTION OF THE DRAWINGS

In the accompanying drawings to which reference is made in the instant specification and which are to be read in conjunction therewith and in which like reference characters are used to indicate like parts in the various views:

FIG. 2 is a schematic view showing a first embodiment of my invention used for measuring high moisture concentrations.

FIG. 3 is a schematic view showing a second embodiment of my invention for measuring lower moisture concentration.

DESCRIPTION OF THE PREFERRED EMBODIMENT

Figures 1, 4:
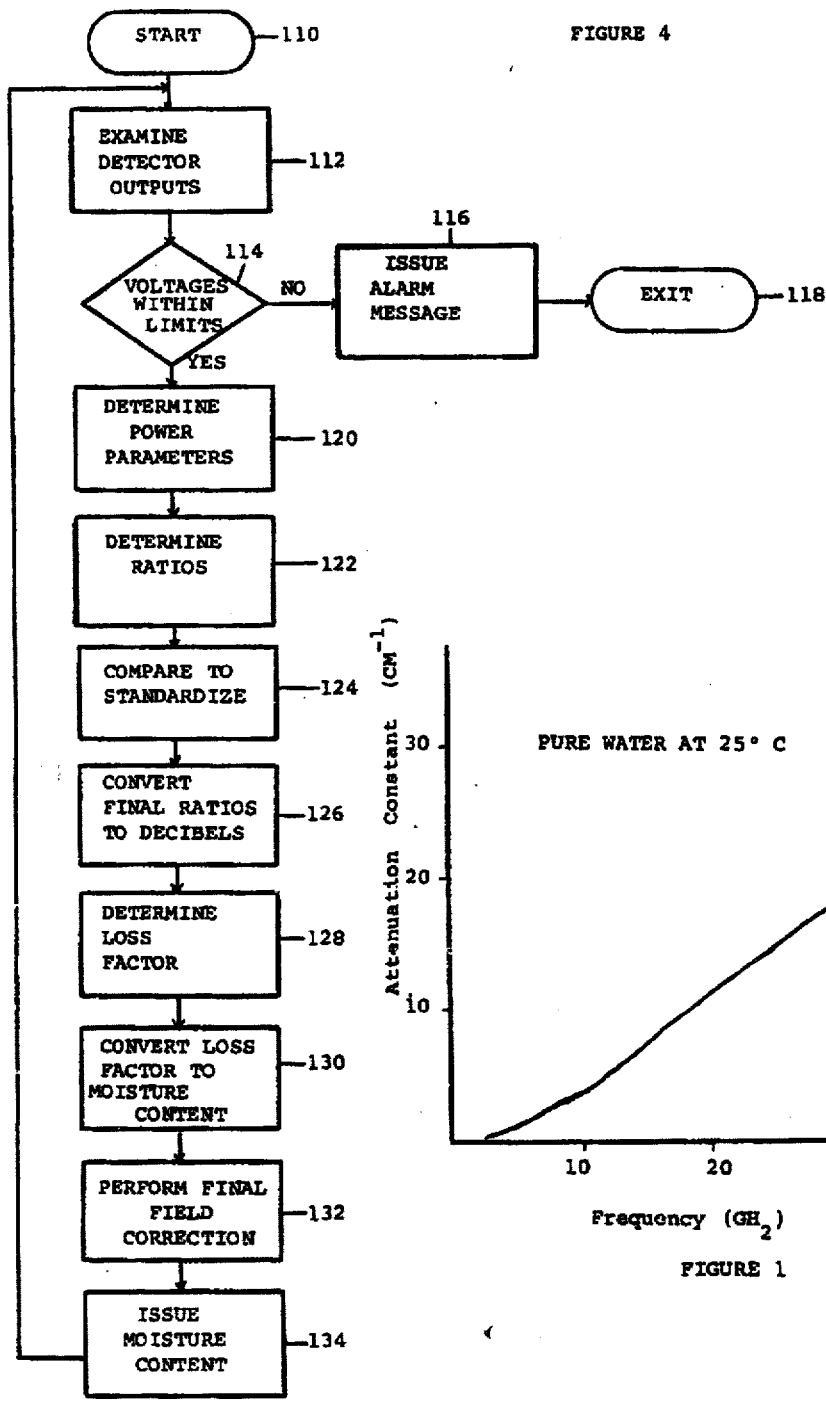
FIG. 1 is a graph illustrating the relationship between frequency and attenuation constant for pure water at 25° C.
FIG. 4 is a flow chart of the routine followed by my invention to determine the moisture content.

Referring now to FIG. 1, it can be seen that the sensitivity of microwaves to water is a function of their frequency. It is, moreover, known that beyond 40 GHz the attenuation constant increases monotonically to 180 GHz (Felix Franks, Physics and Physical Chemistry of Water, Plenum Press, New York 1972).

Referring now to FIG. 2, my microwave moisture sensor 10, shown in the form for measuring high moisture concentrations (above 750 g/m²) in a moving web 12, includes a voltage regulator 14 which supplies power to a standard fixed frequency oscillator 16 through a modulator 18. The oscillator 16 generates microwave radiation in the S or G bands of frequencies, centered about approximately 3.09 GHz or 100 mm wavelength, which passes through an isolator 20 and an attenuator 22 to a directional coupler 24. Isolator 20 prevents energy from being passed backward to oscillator 16 to maintain the stability of the oscillator. Coupler 24 directs a small fraction (about 5%) of the output to a first semiconductor detector 26, which generates a current (or voltage) which is a monotonically increasing function of the intensity of the impinging radiation, providing a reference power signal for both the on ($M_1$) and off ($O_1$) cycle of the modulation. I couple the output of "reference" detector 26 through a preamplifier 28 to a microcomputer 30.

Coupler 24 directs the remaining power through isolator 32 to the first terminal of a microwave circulator 34. Energy entering this terminal is transmitted to a second terminal which is coupled to a transmitting horn antenna 36 positioned beneath the web 12. Transmitting horn 36 directs radiation through the web 12 to a receiving horn antenna 38, placed in alignment with the transmitting horn 36 on the opposite side of the web 12, which collects the radiation not absorbed or scattered by the web. An isolator 40 provides a unidirectional coupling between receiving horn 38 and a second semiconductor detector 42. Detector 42 generates an electrical signal which is a known function of the microwave intensity received by horn 38, which is less than that transmitted by horn 36 owing to the attenuation or absorption by the water molecules in the web 12. Detector 42 provides a transmitted power signal for both the on ($M_2$) and off ($O_2$) cycle of the modulation. I couple the output of "transmission" detector 42 through preamplifier 44 to microcomputer 30.

During operation of my sensor, a certain amount of radiation is reflected from web 12 to transmitting horn 36. This radiation is collected by horn 36 and routed by circulator 34 to a third terminal, coupled to a third semiconductor detector 46, which generates an electrical signal. Detector 46 provides a reflected power signal for both the on ($M_3$) and off ($O_3$) cycle of the modulation. I couple the output of the "reflection" detector 46 to a microcomputer 30 through a preamplifier 48.

An alternate and equally effective configuration for the apparatus is to monitor the reflected radiation via a separate receiving horn aligned to observe the area of the web being irradiated by microwaves from horn 36. In this geometry, circulator 34 is not essential.

The microcomputer obtains voltage outputs from all three preamplifiers 28, 44, and 48 in both the off and on cycle of the modulation, and, in addition, receives an input which is a measure of the basis weight of the web through a suitable detector 50 and an input which is a measure of the temperature of the web through a suitable detector 52, which for example could be a thermistor in direct contact with the web or an optical infrared pyrometer. These measurements are then converted, in a manner to be more fully described hereinbelow, into the web moisture content.

Referring now to FIG. 3, I have shown an alternate embodiment 60 of my microwave moisture sensor adapted for determination of low water concentrations (below 5 g/m²) in a moving web 62. This form of my device includes an oscillator 64 which receives power from a voltage regulator 66 through a pulse modulator 68. To improve the sensitivity of my system to water content below 5 g/m², oscillator 64 generates microwave radiation in the Q band of frequencies centered about approximately 40 GHz or 7.75 mm which is transmitted through isolator 70 to a directional coupler 72. Coupler 72 directs a portion of the power to a first semiconductor detector 74 to provide a reference signal, and the remaining power through isolator 76 to a circulator 78, which routes it to a first transmitting horn 80. Horn 80, positioned above the web, directs the microwave radiation through the web. Radiation which is not absorbed or scattered by the web enters a first receiving horn antenna 82, positioned below the web in alignment with horn 80. The energy received by horn 82 is less than that transmitted by horn 80 because of attenuation or absorption by the water molecules in the web. This energy is then routed to a second transmitting horn 84 which directs the radiation again through the web 62 to a second receiving horn 86. The energy received by horn 86 is less than that transmitted by horn 84 because of attenuation or absorption by the water molecules in the web. An isolator 88 provides a unidirectional coupling between receiving horn 86 and a second semiconductor detector 90, which measures transmitted radiation. By passing the microwaves through the web twice, the sensitivity of the system is greatly improved.

A certain amount of radiation will be reflected from the web 62 to the first transmitting horn 80. This radiation is collected by horn 80 and routed by circulator 78 to a third semiconductor detector 92 which measures reflected radiation. In addition, a certain amount of energy may also be reflected from the first transmitting horn 80 to the second receiving horn 86 and from the second transmitting horn 84 to the first receiving horn 82. Both receiving horns 82 and 86 are cross polarized with respect to the transmitting horns 84 and 80 on their respective sides of the web 62.

I couple the output of the detectors 74, 90 and 92 to a microcomputer 94 through respective preamplifiers 96, 98 and 100. In addition, I supply microcomputer 94 with information as to the temperature and weight of the web through detectors 102 and 104. This information is then converter, in a manner to be more fully described hereinbelow, into the web moisture content.

Referring now to FIG. 4, the routine followed by microcomputer 30 in the embodiment of my invention for measuring high moisture concentrations and microcomputer 94 in the embodiment of my invention for measuring low moisture concentrations begins at block 110. Initially, voltage outputs are obtained from the reference (1), transmission (2) and reflection (3) detectors in both the on and off cycle of the modulation with the web between the transmitting and receiving horns (block 112). If the voltages obtained exceed a preset limit, indicating a malfunction, an alarm message is issued and the program exits the routine (blocks 114, 116 and 118). Otherwise, power parameters $P_1$ for reference, $P_2$ for transmission and $P_3$ for reflection are determined by the formula:

$$P_x = M_x^2 - O_x^2 \qquad (3)$$

where $M_x$ is the voltage obtained in the on cycle of the modulation and $O_x$ is the voltage obtained in the off cycle, from each of the three detectors (block 120).

The parameters are then used to determine the ratios of transmitted power to reference power $R_1 = P_2/P_1$ and reflected power to reference power $R_2 = P_3/P_1$ (block 122). These "on sheet" ratios, with the web between the transmitting and receiving horns, are compared (block 124) to $S_1$ which is the ratio of transmitted to reference power ($S_1 = R_1 = P_2/P_1$) at standardize or "off sheet", with the web removed and nothing between the transmitting and receiving horns. These comparisons are represented by the equations:

$$C_1 = S_1/R_1 \qquad (4)$$

$$C_2 = S_1/R_2 \qquad (5)$$

Value $S_1$ is used for comparison to both ratios $R_1$ and $R_2$ as there is no equivalent "off sheet" measurement for the ratio of reflected power to reference power, or $R_2$ at standardize. It will be readily appreciated that the measurement of the value $S_1$ is determined prior to actual on-line operation of the sensor 10 and stored in the microcomputer.

Ratios $C_1$ and $C_2$ are then converted into decibels $D_1$ and $D_2$ (block 126) and a loss characteristic $D_3$ of both the transmitted and reflected radiation, represented by the equation:

$$D_3 = D_1 + KD_2 \qquad (6)$$

where $K$ is a calibration parameter, which is computed (block 128). The calibration parameter $K$ is used together with the reflection signal $D_2$ to normalize the transmission signal $D_1$, providing a loss factor $D_3$ which is corrected for variations in the thickness of the web. The loss factor $D_3$ is then converted to a web moisture content or a "real moisture" content RM, which is a water weight expressed in engineering units, by the use of a primary calibration table stored in the microcomputer. This "real moisture" content is then further corrected for variations in basis weight and temperature as determined by respective detectors 50 and 52 or 104 and 102. For example, an increase in either basis weight or temperature would correspond to a different moisture content than indicated by the loss factor $D_3$, and the value RM would be adjusted accordingly (block 130).

As indicated by block 132, the real moisture RM or water weight is further corrected by reference to a final field calibration which by the use of free floating parameters, such for example as a slope SL and offset OF, set in the field, renders a final instantaneous moisture value IV, expressed by the equation:

$$IV = SL \times RM + OF \qquad (7)$$

This final calibration is made necessary by the fact that the primary calibration is stored in the microprocessor and may not be easily adjusted in the field. This instantaneous value is then displayed in a suitable manner (block 134) and the program then loops back to block 112.

It will be seen that I have accomplished the objects of my invention. I have provided a microwave moisture sensor which utilizes the reflected microwave energy to provide a moisture content measurement independent of the thickness of the web. My sensor compensates for the effects of variations in the basis weight and temperature of the web on the moisture measurement and is also capable of measuring high moisture content concentrations, above the 750 g/m² and low moisture concentrations below 5 g/m² in a moving web.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what I claim is:

1. Apparatus for measuring the moisture content of a web of material including in combintion means for irradiating said web with microwave energy, means for measuring the intensity of microwave energy transmitted through said web to produce a transmission signal, said transmission signal having a dependence on the thickness of said web, means for measuring the intensity of microwave energy reflected from said web to produce a reflection signal, and means responsive to said reflection signal for correcting said transmission signal for said dependence on the thickness of said web.

2. Apparatus as in claim 1 further comprising means for measuring the intensity of energy emanating from said irradiating means to produce a reference signal and means for normalizing said transmission and reflection signals relative to said reference signal.

3. Apparatus as in claim 1 in which said irradiating means irradiates said web with microwave energy having a frequency of approximately 3 gigahertz.

4. Apparatus as in claim 1 in which said irradiating means irradiates said web with microwave energy having a frequency of aproximately 40 gigahertz.

5. Apparatus as in claim 1 in which said irradiating means directs said energy along a path penetrating said web a plurality of times, said transmission signal means measuring the intensity of energy that has traversed said path.

6. Apparatus as in claim 1 in which said transmission signal has a dependence on the temperature of said web, said apparatus further comprising means for measuring the temperature of said web to provide a temperature signal and means responsive to said temperature signal for correcting said transmission signal for said dependence on the temperature of said web.

7. Apparatus for measuring the moisture content of a web of material including in combination means for irradiating said web with microwave energy, means for measuring the intensity of microwave energy transmitted through said web to produce a transmission signal, said transmission signal having a dependence on the thickness and basis weight of said web, means for producing a thickness signal as a measure of the thickness of said web, means for producing a basis weight signal independent of said thickness signal as a measure of the basis weight of said web, and means responsive to said basis weight and thickness signals for independently correcting said transmission signal for said dependence on the thickness and basis weight of said web.

8. Apparatus as in claim 7 in which said means for producing said thickness signal includes means for measuring the intensity of microwave energy reflected from the web.

9. Apparatus for measuring the moisture content of a web of material including in combination a first microwave antenna arranged to direct microwave energy through said web, a second microwave antenna arranged to receive microwave energy from said first antenna that has penetrated said web, means for supplying microwave energy to said first antenna, means for measuring the intensity of microwave energy received by said second antenna to produce a transmission signal, said transmission signal having a dependence on the thickness of said web, means for measuring the intensity of microwave energy reflected from said web back to said first antenna to produce a reflection signal, and means responsive to said reflection signal for correcting said transmission signal for said dependence on the thickness of said web.

10. Apparatus as in claim 9 further comprising means for measuring the energy supplied to said first antenna to produce a reference signal and means for normalizing said transmission and reflection signals relative to said reference signal.

* * * * *